(12) United States Patent
Achter et al.

(10) Patent No.: US 7,514,270 B2
(45) Date of Patent: Apr. 7, 2009

(54) IMMUNOASSAY PROBE

(75) Inventors: Eugene K. Achter, Lexington, MA (US); Hartmut Richard Schroeder, Franklin, MA (US); Stephen S. Trotta, Woburn, MA (US)

(73) Assignee: Instrumentation Laboratory Company, Lexington, MA (US)

( * ) Notice: Subject to any disclaimer, the term of this patent is extended or adjusted under 35 U.S.C. 154(b) by 1063 days.

(21) Appl. No.: 10/411,441

(22) Filed: Apr. 10, 2003

(65) Prior Publication Data

US 2003/0194799 A1 Oct. 16, 2003

Related U.S. Application Data

(60) Provisional application No. 60/372,331, filed on Apr. 12, 2002.

(51) Int. Cl.
*G01N 33/553* (2006.01)
*G01N 21/00* (2006.01)

(52) U.S. Cl. .................. 436/526; 436/47; 436/807; 422/65; 422/68.1; 209/214; 210/222; 210/695

(58) Field of Classification Search ................. 436/526, 436/47, 807; 209/214; 210/222, 695; 422/65, 422/68.1
See application file for complete search history.

(56) References Cited

U.S. PATENT DOCUMENTS

| | | | |
|---|---|---|---|
| 3,932,131 A | 1/1976 | Rolfo-Fontana | 23/230 R |
| 3,939,834 A | 2/1976 | McMahon | 128/272 |
| 3,952,599 A | 4/1976 | Ayres | 73/425.4 P |
| 3,985,649 A | 10/1976 | Eddelman | 210/42 |
| 3,992,150 A | 11/1976 | Retzer | 23/230 |
| 4,022,577 A | 5/1977 | Brooker et al. | 23/230 B |
| 4,037,464 A | 7/1977 | Wenander | 73/61.4 |
| 4,046,515 A | 9/1977 | de Leeuw | 23/259 |
| 4,058,370 A | 11/1977 | Suovaniemi | 23/259 |
| 4,066,407 A | 1/1978 | Lupica | 23/230 B |
| 4,067,776 A | 1/1978 | Khan | 195/103.5 M |

(Continued)

FOREIGN PATENT DOCUMENTS

EP 0638809 A2 2/1995

(Continued)

OTHER PUBLICATIONS

Doyle et al., "Self-Assembled Magnetic Matrices for DNA Separation Chips," Science vol. 295, Mar. 22, 2002 at. 2297.

(Continued)

*Primary Examiner*—Mark L Shibuya
*Assistant Examiner*—Pensee T Do
(74) *Attorney, Agent, or Firm*—K&L Gates LLP (57) ABSTRACT

An analytical instrument for the immobilization of antigens to be detected in an immunoassay using mangetizable beads. The instrument includes a probe containing magnetizable particles and a plurality of magnetic devices for applying a magnetic field gradient to the particles in the probe reservoir. The probe is movable between the plurality of magnetic devices and at least one of the probe positions may be used to immobilize the magnetic particles in the fluid medium and at least another position may be used to resuspend the particles in a fluid medium.

4 Claims, 9 Drawing Sheets

U.S. PATENT DOCUMENTS

| | | | |
|---|---|---|---|
| 4,141,687 A | 2/1979 | Forrest et al. ............. 23/230 R |
| 4,195,526 A | 4/1980 | Amos et al. ............... 73/425.6 |
| 4,243,684 A | 1/1981 | Pruss et al. .................. 426/40 |
| 4,275,591 A | 6/1981 | Wand ..................... 73/864.01 |
| 4,292,920 A | 10/1981 | Smith et al. ................ 118/425 |
| 4,361,032 A | 11/1982 | Lessnig et al. .............. 73/64.4 |
| 4,483,825 A | 11/1984 | Fatches ..................... 422/100 |
| 4,526,046 A | 7/1985 | Oberli .................... 73/864.16 |
| 4,567,149 A | 1/1986 | Sell et al. ................... 436/513 |
| 4,592,338 A | 6/1986 | Blackmore ................ 128/1 R |
| 4,622,847 A | 11/1986 | Paoletti et al. .............. 73/61.4 |
| 4,677,067 A | 6/1987 | Schwartz et al. ............ 435/177 |
| 4,692,609 A | 9/1987 | Pettersson .................. 250/221 |
| 4,699,881 A | 10/1987 | Matschke ................... 435/173 |
| 4,701,418 A | 10/1987 | Katopodis ................... 436/64 |
| 4,710,472 A * | 12/1987 | Saur et al. ................ 435/308.1 |
| 4,721,680 A | 1/1988 | Jeffs et al. .................. 436/180 |
| 4,748,128 A | 5/1988 | Katopodis ................... 436/93 |
| 4,783,250 A | 11/1988 | Pons et al. .................. 204/400 |
| 4,790,176 A | 12/1988 | Marteau d'Autry ........... 73/1 H |
| 4,793,973 A | 12/1988 | Ringrose ..................... 422/102 |
| 4,795,698 A | 1/1989 | Owen et al. ..................... 435/4 |
| 4,798,705 A | 1/1989 | Jakubowicz et al. .......... 422/63 |
| 4,830,832 A | 5/1989 | Arpagaus et al. ............. 422/65 |
| 4,873,875 A | 10/1989 | Cork ....................... 73/863.01 |
| 4,895,650 A | 1/1990 | Wang ......................... 210/222 |
| 4,904,396 A | 2/1990 | Benet ......................... 210/745 |
| 4,929,427 A | 5/1990 | Guala ......................... 422/100 |
| 4,931,257 A | 6/1990 | Quenin et al. ................ 422/100 |
| 4,933,291 A | 6/1990 | Daiss et al. ................... 436/45 |
| 4,962,044 A | 10/1990 | Knesel, Jr. et al. .......... 436/177 |
| 4,970,892 A | 11/1990 | Enhorning .................. 73/64.4 |
| 4,988,618 A | 1/1991 | Li et al. ......................... 435/6 |
| 5,009,847 A | 4/1991 | Solomons .................... 422/61 |
| 5,010,930 A | 4/1991 | Columbus ..................... 141/1 |
| 5,013,529 A | 5/1991 | Itoh ............................ 422/100 |
| 5,026,526 A | 6/1991 | Quenin et al. ................. 422/64 |
| 5,045,453 A | 9/1991 | Katopodis .................... 435/18 |
| 5,068,089 A | 11/1991 | Ericsson et al. ............... 422/61 |
| 5,084,041 A | 1/1992 | Oxley et al. ................. 604/410 |
| 5,104,621 A | 4/1992 | Pfost et al. ................... 422/67 |
| 5,106,584 A | 4/1992 | Funakubo et al. ............. 422/65 |
| 5,110,727 A | 5/1992 | Oberhardt .................... 435/13 |
| 5,122,342 A | 6/1992 | McCulloch et al. ............ 422/65 |
| 5,128,103 A | 7/1992 | Wang et al. ................... 422/64 |
| 5,137,352 A | 8/1992 | Blitshteyn et al. ........... 356/138 |
| 5,138,868 A | 8/1992 | Long ............................ 73/1 R |
| 5,141,871 A | 8/1992 | Kureshy et al. ............... 436/47 |
| 5,147,529 A | 9/1992 | Lee et al. |
| 5,156,948 A | 10/1992 | Christensen et al. ........... 435/5 |
| 5,160,329 A | 11/1992 | Oxley ......................... 604/317 |
| 5,160,378 A | 11/1992 | Tuunanen et al. .......... 134/25.1 |
| 5,171,537 A | 12/1992 | Wainwright et al. ........ 422/100 |
| 5,175,086 A | 12/1992 | Takekawa et al. |
| 5,183,638 A | 2/1993 | Wakatake .................... 422/64 |
| 5,186,827 A | 2/1993 | Liberti et al. ................ 210/222 |
| 5,200,084 A | 4/1993 | Liberti et al. ................ 210/695 |
| 5,200,151 A | 4/1993 | Long .......................... 422/100 |
| 5,232,665 A | 8/1993 | Burkovich et al. ............ 422/65 |
| 5,250,262 A | 10/1993 | Heidt et al. ................... 422/64 |
| 5,262,325 A | 11/1993 | Zimmermann et al. ...... 435/269 |
| 5,268,147 A | 12/1993 | Zabetakis et al. ............. 422/82 |
| 5,270,210 A | 12/1993 | Weyrauch et al. ............. 436/43 |
| 5,289,385 A | 2/1994 | Grandone ................... 364/497 |
| 5,296,194 A | 3/1994 | Igarashi ................... 422/82.05 |
| 5,334,538 A | 8/1994 | Parker et al. ................ 436/525 |
| 5,340,749 A | 8/1994 | Fujiwara et al. ............. 436/526 |
| 5,344,610 A | 9/1994 | Shaw ......................... 422/100 |
| 5,399,497 A | 3/1995 | Kumar et al. ................ 436/53 |
| 5,403,707 A | 4/1995 | Atwood et al. ................. 435/5 |
| 5,407,798 A | 4/1995 | Martinelli et al. .............. 435/6 |
| 5,411,072 A | 5/1995 | Starck et al. ............. 160/84.11 |
| 5,411,863 A | 5/1995 | Miltenyi ........................ 435/6 |
| 5,422,075 A | 6/1995 | Saito et al. .................... 422/52 |
| 5,433,716 A | 7/1995 | Leopardi et al. ............. 604/415 |
| 5,437,979 A | 8/1995 | Rampal et al. .................. 435/6 |
| 5,453,619 A | 9/1995 | Asselain et al. .......... 250/339.12 |
| 5,458,785 A | 10/1995 | Howe et al. ................. 210/695 |
| 5,466,574 A | 11/1995 | Liberti et al. ................... 435/5 |
| 5,482,861 A | 1/1996 | Clark et al. ................... 436/48 |
| 5,482,864 A | 1/1996 | Knobel ......................... 436/54 |
| 5,489,532 A | 2/1996 | Charm et al. ............. 435/286.1 |
| 5,498,550 A | 3/1996 | Fujiwara et al. ............. 436/526 |
| 5,536,475 A | 7/1996 | Moubayed et al. .......... 422/101 |
| 5,541,072 A | 7/1996 | Wang et al. ................. 435/7.21 |
| 5,565,365 A | 10/1996 | Glass .......................... 436/526 |
| 5,565,366 A | 10/1996 | Akers, Jr. ................... 436/534 |
| 5,578,270 A | 11/1996 | Reichler et al. ................ 422/67 |
| 5,580,524 A | 12/1996 | Forrest et al. .................. 422/63 |
| 5,589,350 A | 12/1996 | Bochner ...................... 435/29 |
| 5,595,913 A | 1/1997 | Lawlor et al. ................. 436/17 |
| 5,597,531 A | 1/1997 | Liberti et al. ................. 423/57 |
| 5,599,501 A | 2/1997 | Carey et al. ................... 422/64 |
| 5,607,766 A | 3/1997 | Berger ....................... 428/373 |
| 5,620,898 A | 4/1997 | Yaremko et al. ............... 436/45 |
| 5,622,831 A | 4/1997 | Liberti et al. ............... 435/7.21 |
| 5,646,047 A | 7/1997 | Bird et al. .................... 436/128 |
| 5,647,994 A * | 7/1997 | Tuunanen et al. ............ 210/695 |
| 5,681,478 A | 10/1997 | Lea et al. ..................... 210/695 |
| 5,702,950 A | 12/1997 | Tajima ......................... 436/49 |
| 5,705,062 A | 1/1998 | Knobel ....................... 210/205 |
| 5,741,708 A | 4/1998 | Carey et al. ................... 436/49 |
| 5,789,167 A | 8/1998 | Konrad ......................... 435/6 |
| 5,827,478 A | 10/1998 | Carey et al. ................... 422/64 |
| 5,834,197 A | 11/1998 | Parton ............................ 435/6 |
| 5,837,144 A | 11/1998 | Bienhaus et al. ............. 210/695 |
| 5,843,312 A | 12/1998 | Manz et al. ................. 210/635 |
| 5,849,247 A | 12/1998 | Uzan et al. .................... 422/65 |
| 5,877,035 A | 3/1999 | Fujino et al. ................... 438/16 |
| 5,885,529 A | 3/1999 | Babson et al. |
| 5,885,530 A | 3/1999 | Babson et al. ................. 422/65 |
| 5,888,758 A | 3/1999 | Wu ............................... 435/28 |
| 5,888,835 A | 3/1999 | Bushnell et al. ............. 436/526 |
| 5,895,631 A | 4/1999 | Tajima ........................ 422/101 |
| 5,897,783 A | 4/1999 | Howe et al. ................. 210/695 |
| 5,910,122 A | 6/1999 | D'Angelo .................... 600/573 |
| 5,919,706 A | 7/1999 | Tajima ......................... 436/54 |
| 5,922,284 A | 7/1999 | Kinoshita et al. ........... 422/68.1 |
| 5,932,299 A | 8/1999 | Katoot ........................ 427/508 |
| D414,562 S | 9/1999 | Tajima ......................... 24/222 |
| 5,952,233 A | 9/1999 | Pellet et al. ..................... 436/6 |
| 5,976,369 A | 11/1999 | Howe et al. ................. 210/222 |
| 5,985,153 A | 11/1999 | Dolan et al. ................. 210/695 |
| 5,985,671 A | 11/1999 | Leistner et al. ................ 436/49 |
| 5,993,665 A | 11/1999 | Terstappen et al. .......... 210/695 |
| 6,001,573 A | 12/1999 | Roelant ......................... 435/6 |
| 6,006,800 A | 12/1999 | Nakano ....................... 141/130 |
| 6,008,010 A | 12/1999 | Greenberger et al. ......... 435/41 |
| 6,013,188 A | 1/2000 | Terstappen et al. .......... 210/695 |
| 6,020,211 A | 2/2000 | Tuunanen .................... 436/526 |
| 6,040,192 A | 3/2000 | Tuunanen .................... 436/177 |
| 6,043,205 A | 3/2000 | Hoshiko et al. .............. 510/161 |
| 6,063,260 A | 5/2000 | Olesen et al. ................ 205/793 |
| 6,065,605 A | 5/2000 | Korpela et al. |
| 6,066,297 A | 5/2000 | Torti et al. ................... 422/100 |
| 6,074,609 A | 6/2000 | Gavin et al. ................... 422/99 |
| 6,096,554 A | 8/2000 | Tajima ......................... 436/49 |
| 6,100,079 A | 8/2000 | Tajima ........................ 435/239 |
| 6,100,094 A | 8/2000 | Tajima ......................... 436/54 |
| 6,114,292 A | 9/2000 | Hoshiko et al. .............. 510/161 |
| 6,117,398 A | 9/2000 | Bienhaus et al. ............. 422/101 |
| 6,123,903 A | 9/2000 | Tajima ......................... 422/52 |
| 6,124,142 A | 9/2000 | Fujino et al. ................... 438/18 |
| 6,133,037 A | 10/2000 | Tajima ......................... 436/49 |

| | | | |
|---|---|---|---|
| 6,136,182 A | 10/2000 | Dolan et al. .................. 210/94 |
| 6,143,250 A | 11/2000 | Tajima ....................... 422/102 |
| 6,143,578 A * | 11/2000 | Bendele et al. ............. 436/526 |
| 6,146,838 A | 11/2000 | Williams et al. ............. 435/7.2 |
| 6,150,182 A | 11/2000 | Cassaday ................... 436/526 |
| 6,174,668 B1 | 1/2001 | Cummins et al. ............. 435/6 |
| 6,187,270 B1 | 2/2001 | Schmitt et al. ............. 422/101 |
| 6,193,892 B1 | 2/2001 | Krueger et al. ............. 210/695 |
| 6,225,061 B1 | 5/2001 | Becker et al. ................. 435/6 |
| 6,225,126 B1 | 5/2001 | Cohen et al. ................. 436/69 |
| 6,225,128 B1 | 5/2001 | White ........................ 436/77 |
| 6,231,814 B1 | 5/2001 | Tajima ....................... 422/101 |
| 6,232,124 B1 | 5/2001 | Selinfreund ................. 436/20 |
| 6,255,051 B1 | 7/2001 | Hammond et al. ............. 435/6 |
| 6,268,209 B1 | 7/2001 | Pierson et al. ........... 435/287.9 |
| 6,277,332 B1 | 8/2001 | Sucholeiki .................. 422/128 |
| 6,291,249 B1 | 9/2001 | Mahant et al. .............. 436/177 |
| 6,328,934 B1 | 12/2001 | Ljung et al. ................. 422/119 |
| 6,331,277 B2 | 12/2001 | Tajima ....................... 422/100 |
| 6,333,008 B1 | 12/2001 | Leistner et al. |
| 6,335,166 B1 | 1/2002 | Ammann et al. ............... 435/6 |
| 6,337,053 B1 | 1/2002 | Tajima ....................... 422/102 |
| 6,346,408 B1 | 2/2002 | Chuch ........................ 435/238 |
| 6,368,872 B1 | 4/2002 | Juranas ...................... 436/180 |
| 6,370,942 B1 | 4/2002 | Dunfee et al. .................. 73/37 |
| 6,372,183 B1 | 4/2002 | Akong et al. ................. 422/63 |
| 6,372,185 B1 | 4/2002 | Shumate et al. ............. 422/100 |
| 6,396,584 B1 | 5/2002 | Taguchi et al. .............. 356/436 |
| 6,409,925 B1 | 6/2002 | Gombinsky et al. ......... 210/695 |
| 6,417,011 B1 * | 7/2002 | Miltenyi ..................... 436/526 |
| 6,444,171 B1 | 9/2002 | Sakazume et al. ............. 422/65 |
| 6,447,729 B1 | 9/2002 | Tuunanen .................. 422/101 |
| 6,448,092 B1 | 9/2002 | Tuunanen .................. 436/526 |
| 6,455,325 B1 | 9/2002 | Tajima ....................... 436/526 |
| 6,461,808 B1 | 10/2002 | Bodner et al. .................. 435/4 |
| 6,468,810 B1 | 10/2002 | Korpela ....................... 436/526 |
| 6,470,279 B1 | 10/2002 | Samsoondar ................. 702/28 |
| 6,471,917 B1 | 10/2002 | Velkovska et al. .......... 422/100 |
| 6,482,328 B1 | 11/2002 | Davidson et al. ............. 210/695 |
| 6,500,343 B2 | 12/2002 | Siddiqi ....................... 210/695 |
| 6,509,193 B1 | 1/2003 | Tajima ......................... 436/49 |
| 6,517,783 B2 | 2/2003 | Horner et al. ............... 422/102 |
| 6,537,505 B1 | 3/2003 | LaBudde et al. ............. 422/103 |
| 6,543,515 B2 | 4/2003 | Hummell et al. ............. 156/556 |
| 6,569,204 B1 | 5/2003 | Aldecoa .................... 623/23.51 |
| 6,572,778 B2 | 6/2003 | Sterman et al. ............. 210/695 |
| 6,573,088 B2 | 6/2003 | Gemmell et al. ......... 435/286.4 |
| 6,579,453 B1 | 6/2003 | Bächler et al. .............. 210/222 |
| 6,597,176 B2 | 7/2003 | Simmonds et al. .......... 324/326 |
| 6,602,422 B1 | 8/2003 | Miltenyi et al. ............. 210/695 |
| 6,605,213 B1 | 8/2003 | Ammann et al. ............. 210/222 |
| 6,610,186 B1 | 8/2003 | Mayer et al. ................. 204/451 |
| 6,649,419 B1 | 11/2003 | Anderson |
| 6,660,159 B1 | 12/2003 | Terstappen et al. |
| 6,672,458 B2 | 1/2004 | Hansen et al. |
| 6,691,748 B1 | 2/2004 | Tajima |
| 6,723,237 B1 | 4/2004 | Tajima |
| 6,764,859 B1 | 7/2004 | Kreuwel et al. |
| 6,790,366 B2 | 9/2004 | Terstappen et al. |
| 6,805,840 B1 | 10/2004 | Tajima |
| 6,884,357 B2 | 4/2005 | Siddiqi |
| 2001/0007312 A1 | 7/2001 | Siddiqi ....................... 210/695 |
| 2001/0007770 A1 | 7/2001 | Tajima ......................... 436/47 |
| 2001/0016178 A1 | 8/2001 | Acosta et al. ............... 422/100 |
| 2002/0008053 A1 | 1/2002 | Hansen et al. ................. 209/8 |
| 2002/0048534 A1 | 4/2002 | Storek et al. .................. 422/99 |
| 2002/0048821 A1 | 4/2002 | Storek et al. ................. 436/174 |
| 2003/0012699 A1 | 1/2003 | Moore et al. ................. 422/100 |
| 2003/0049171 A1 | 3/2003 | Tamura et al. ................. 422/64 |
| 2003/0215361 A1 | 11/2003 | Jang |
| 2004/0004043 A1 | 1/2004 | Terstappen et al. |
| 2004/0029291 A1 | 2/2004 | Franzreb et al. |
| 2004/0047765 A1 | 3/2004 | Gordon et al. |
| 2004/0265173 A1 | 12/2004 | Matsumoto et al. |
| 2004/0265903 A1 | 12/2004 | Mueller et al. |
| 2005/0013741 A1 | 1/2005 | a'Brassard |
| 2005/0047963 A1 | 3/2005 | Safar et al. |
| 2005/0084423 A1 | 4/2005 | Zarowitz et al. |

FOREIGN PATENT DOCUMENTS

| | | |
|---|---|---|
| WO | WO95/00247 | 6/1994 |
| WO | WO 02/44725 A1 | 6/2002 |

OTHER PUBLICATIONS

European Search Report for European Patent Application for EP 0638809 A2, Dec. 9, 1996.

Patent Cooperation Treaty (PCT) International Search Report (PCT Article 18 and Rules 43 and 44), International Application No. PCT/US03/11157, International Filing Date: Oct. 4, 2003, Applicant: Instrumentation Laboratory Company.

Boehringer Mannheim Biochemicals, "Magnetic protAspheres," BMBiochemica, 1984, vol. 1 No. 3, pp. 1-2.

Landon, "Magneitsable Particles in Immunochemistry," 1982, Technical Publication of Worldwide Technical Marketing, Corning Medical, Medfield, Massachusetts, pp. 1-5. (Please note: Applicant best estimates 1982 as the year when this document became publicly available.).

McNicol et al., "Automation of Dupont's Chromium Dioxide Magnetic Particle Based Immunoassays," pp. 1-19, presented Apr. 13-14, 1988, in Savannah, Georgia, at the Oakridge Meeting of the Association for Clinical Chemists.

Nye et al., "Solid-Phase, Magnetic Particle Radioimmunoassay," Clinica Chimica Acta, 1976, vol. 69, pp. 387-396.

Guesdon et al., "Magnetic Solid Phase Enzyme-Immunoassay," Immunochemistry, 1977, vol. 14, pp. 443-447.

Ng et al., "Performance of Five Thyroid-Function Tests by Radioimmunoassays with Antibodies Attached to Paramagnetic Micro-Particles," Clinical Chemistry, 1985, vol. 31 No. 1, pp. 87-90.

Piran et al., "Immunochemiluminometric Assay of Creatine Kinase MB with a Monoclonal Antibody to the MB Isoenzyme," Clinical Chemistry, 1987, vol. 33 No. 9, pp. 1517-1520.

Sturgess et al., "Chemiluminescent Labeled-Antibody Assay for Thyroxin in Serum, with Magnetic Separation of the Solid-Phase," Clinical Chemistry, 1986, vol. 32 No. 3, pp. 532-535.

"Chemilumineszenz . . . bringt Licht ins Labor," Publication of Ciba-Corning Diagnostics GmbH, 1996, pp. 1-11, Presented at the 4th International Bioluminescence and Chemiluminescence Symposium, Freiburg, Germany, Sep. 1986. Original German language publication and English translation.

Weeks et al. "Chemiluminescence Immunoassay," Journal of Clinical Immunoassay, Spring 1984, vol. 7 No. 1, pp. 82-89.

* cited by examiner

IMMUNOASSAY PROBE

CROSS REFERENCE TO RELATED APPLICATION

This application is based on and claims priority to provisional U.S. Application No. 60/372,331 which was filed on Apr. 12, 2002.

TECHNICAL FIELD OF THE INVENTION

This invention relates to clinical diagnostic assays, in particular, immunoassays utilizing magnetizable particles and methods thereof.

BACKGROUND OF THE INVENTION

Immunoassays, such as chemiluminescent immunoassays, generally require two antibody preparations, a first antibody used to capture and immobilize a target antigen molecule, and a second antibody used to attach a detection label to the antigen.

Immobilization of the antigen to be detected in an immunoassay may be accomplished using magnetizable beads, and detection may be accomplished by using a suitable visualant such as isoluminol chemiluminescence. The assay involves the following major steps. For example, a sample containing the antigen is mixed with a first antibody to the antigen which is coupled to magnetizable latex beads, and the mixture is allowed to react. A second antibody, typically to a different epitope on the antigen, coupled to isoluminol, is added to the sample in step 1 and the mixture is allowed to react. A magnetic field is applied to retain the magnetizable beads (with antigen bound, labeled antibody) against the inside wall of the container. A wash fluid is introduced to remove the unbound labeled antibody. Washing the magnetizable beads typically occurs by immobilizing the beads in the magnetic field, introducing a wash fluid, removing the magnetic field, and repeatedly expelling beads into and aspirating the beads from a container to recover all of the beads and to homogeneously mix and resuspend the beads in the wash fluid. The magnetizable beads with antigen bound, labeled antibody are resuspended in a suitable optical cuvette. An activating reagent such as hydrogen peroxide which activates isoluminol is added with the beads in the cuvette and light is emitted in a chemiluminescent reaction. The light emitted from the chemiluminescent reaction is detected using a suitable photodetector. For some applications, additional steps of reagent addition and/or washing may be necessary.

SUMMARY OF THE INVENTION

The invention described herein features an analytical instrument including a probe with a reservoir, a dilutor assembly for introducing fluid containing magnetizable particles into the probe reservoir, and a plurality of magnetic devices for applying a magnetic field gradient to the particles in the probe reservoir. In one embodiment according to the invention, the analytical instrument has a magnetic washing station and a sampling station. The probe containing magnetic particles in the probe reservoir is moved into the magnetic washing station, that includes the magnets. The magnets include, for example, at least a first magnet and a second magnet, the second magnet having a magnetic field of different magnitude than the first magnet. Other magnetic devices are contemplated by the invention, such as one or more solenoid coils, and are not limited to the magnetic devices decried herein.

In one aspect, the invention includes a device for manipulating a magnetizable particle in a fluid medium. In one embodiment, according to the invention, the device may be used in an analytical instrument for determining the presence or measuring the quantity of an analyte in body fluids. The device includes a probe for holding and transporting the magnetizable particles and the probe is transportable to a plurality of positions. The device further includes a first magnet for generating a first magnetic field, and a second magnet for generating a second magnetic field. The probe is moveable in a plurality of probe positions between the first and second magnets. At least one of the probe positions immobilizes the magnetic particles in the fluid medium and at least another position resuspends the particles in a fluid medium. In one embodiment, the magnetizable beads are immobilized against an inner wall of the probe. The inner wall of the probe may be curved or flat.

In one embodiment, the magnitude of the first magnetic field is different than the magnitude of the second magnetic field. In a particular embodiment, the first magnet is in the range of about 1 to 5 times the strength of the second magnet. In a particular embodiment, the first magnet is in the range of about 1 to 2 times the strength of the second magnet. In yet another embodiment of the invention, the first magnet is separated from the second magnet by a gap in the range of about 1/16 inch to 40 inches, preferably, 1.5 to 2.5 inches, more preferably 1.95 inches.

In one embodiment there are three probe positions. The probe positions include a neutral position, an immobilizing position, and a resuspend position. In one embodiment the device has a transport stage for moving the probe between the plurality of probe positions. The transport stage may also move the probe between a sample station and a magnetic washing station. In a particular embodiment the probe has a thermal control element, and/or a liquid sensing element.

In one embodiment according to the invention, the device has a dilutor assembly for introducing a fluid from a fluid reservoir into the probe reservoir through the top end of the probe. The top end of the probe is opposite to an end of the probe used for receiving a sample. In another embodiment, the dilutor assembly introduces fluid to the sample end of the probe.

In another aspect, the invention is a method for washing a magnetizable particle including the steps of aspirating a fluid sample comprising magnetizable particles into a probe. The probe has a top end that is opposite to an end of said probe for receiving a sample. The probe is transported by the transport stage to a magnetic washing station. The magnetic washing station has a first magnet for generating a first magnetic field and a second magnet for generating a second magnetic field. The probe is moved in the magnetic washing station to a capture position, and then to a resuspend position. The magnetizable particles are expelled from the probe. In yet another embodiment of the invention, the resuspend position is closer to the second magnet than the neutral position.

In one embodiment according to the invention, the lumen of the probe is flushed in the capture position with a diluent from a diluter assembly. The diluent for flushing may be introduced at a second end of the probe and expelled at a first end of the probe.

In one embodiment according to the invention, the magnetizable particles are expelled into a container which may be a microtiter well.

In another aspect, the magnetizable particles are incubated with a body fluid and/or an immunoassay is performed.

These and other objects, along with advantages and features of the present invention herein disclosed, will become apparent through reference to the following description, the accompanying drawings and the claims. Furthermore, it is to be understood that the features of the various embodiments described herein are not mutually exclusive and can exist in various combinations and permutations.

BRIEF DESCRIPTION OF THE FIGURES

The foregoing and other objects, features and advantages of the present invention disclosed herein, as well as the invention itself, will be more fully understood from the following description of preferred embodiments and claims, when read together with the accompanying drawings. The drawings are not to drawn to scale and emphasis instead is generally being placed upon illustrating the principles of the invention.

DESCRIPTION OF THE INVENTION

The invention, described herein, is a device, such as a clinical analytical instrument, including a washing probe for use in analyzing fluids, such as blood, in assays using magnetizable particles. The embodiments of the invention described below have the following common features, a transportable probe that has a reservoir for holding a fluid medium containing a plurality of magnetizable particles, at least two magnets, and a probe transport stage. The probe is moveable by the transport stage in a plurality of positions with respect to at least one magnet. The plurality of probe positions with respect to at least one magnet repositions the magnetizable particles in the probe reservoir between at least a capture position and a resuspend position.

In general, the invention is a device having a probe that serves as a reservoir for washing, rinsing, or otherwise manipulating magnetizable particles, such as beads, in a fluid medium such as a suspension or a solution.

Figure 1:
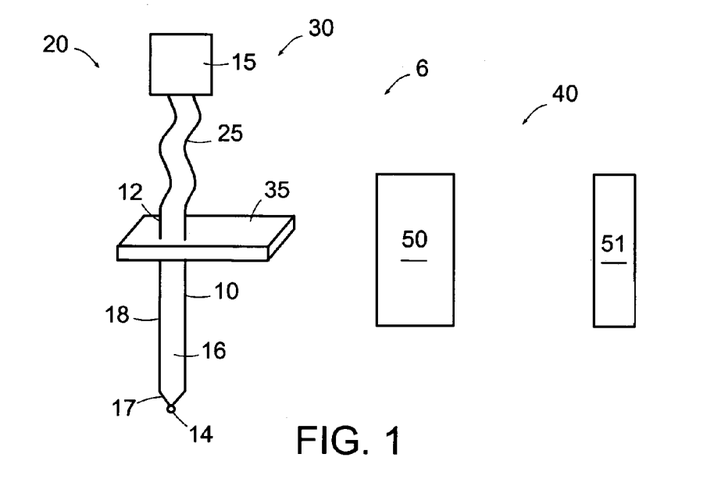
FIG. 1 illustrates an embodiment of the device according to the invention.
Figure 2A:
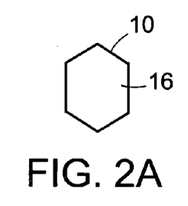
FIGS. 2A-2D illustrates in cross-section, various embodiments of the probe according to the invention.
Figure 2B:
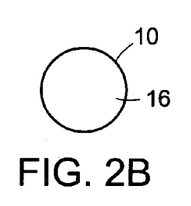
Figure 2C:
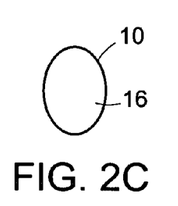
Figure 2D:
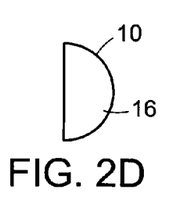

Referring to FIG. 1, in one embodiment according to the invention, the device 6 includes a probe assembly 30, a sampling station 20 and a magnetic washing station 40. The probe assembly 30 has a probe 10 in combination with a dilutor assembly 15, flexible tubing 25, and transport stage 35. The probe 10, illustrated in FIG. 1, is generally a hollow tube having a top end 12, a sample end 14 opposite to the top end 12, a reservoir 16 extending along at least a portion of the length of the probe 10 from the top end 12 to the sample end 14, and at least one probe wall 18. In one embodiment, the probe 10 is substantially straight, rigid and has a round cross-section. In another embodiment according to the invention, for example, illustrated in FIG. 2A, a cross-section of the probe 10 is polygonal and at least one wall of the probe 10 is flat. In yet another embodiment according to the invention, illustrated in FIGS. 2B-2D, a cross-section of the probe 10 is round, oval, or D-shaped.

In a particular embodiment of the probe 10 according to the invention, the sample end 14 of the probe may terminate in a nozzle 17, illustrated in FIG. 1, having a cross-sectional diameter that is smaller than the reservoir 16 of the probe 10. The nozzle 17 increases the velocity of the fluid expelled from the sample end 14 of the probe 10. The shape of the probe 10 is not limited to those illustrated and may include other shapes. The probe 10 may be manufactured from non-magnetic materials such as glass, plastic, ceramics, composite materials, metals, metal alloys, or other materials known to one skilled in the art. The probe 10 may be manufactured from one material and clad in another material or may be made from multiple layers of the same material.

Referring still to FIG. 1, the dilutor assembly 15 is operatively joined to the top end 12 of the probe 10 by tubing 25, such as flexible tubing. In one embodiment, the dilutor assembly 15, for example, is a syringe pump with a rotary directional valve. The dilutor assembly 15 pumps fluid such as a diluent or a wash fluid from a container (not shown) into the tubing 25, through the top end 12 of the probe 10, into the reservoir 16 of the probe 10, and dispenses the fluid out of the probe 10 through the sample end 14. The syringe pump may be optionally ported via the flexible tubing 25 to the probe 10, or to a container of fluid (not shown) upstream from the probe 10. The dilutor assembly 15 may also be an aspirator for aspirating fluid, for example, sample fluid such as body fluids, through the sample end 14 of the probe 10 into the reservoir 16 of the probe 10.

The tubing 25 connecting the dilutor assembly 15 to the probe 10 is manufactured from polytetrafluoroethylene, rubber, polyvinylchloride, polyethylene, or other materials known in the art.

With continued reference to FIG. 1, the probe assembly 30 further includes a transport stage 35 to which the probe 10 is joined. The three axis transport stage 35 moves the probe 10 in a plurality of directions including at least bi-directional horizontal and bi-directional vertical movement.

Alternatively, the transport stage 35 may have a vertical motion that moves the probe 10 vertically, a horizontal motion that moves the probe 10 horizontally and/or a rotary motion that swings the probe 10 in an arc.

Figure 3:
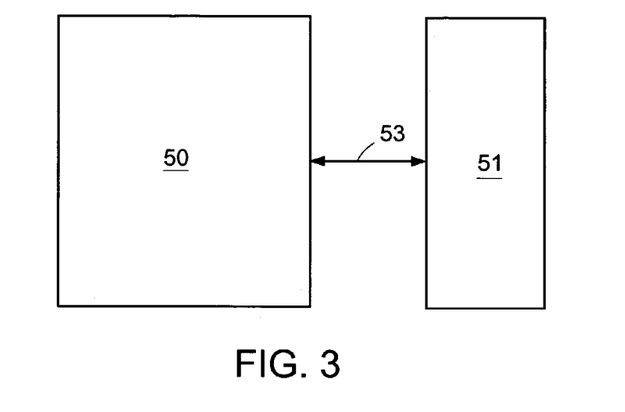
FIG. 3 illustrates one embodiment of the relative positioning of a first magnet to a second magnet in the magnetic washing station according to the invention.

Referring now to FIG. 3, the magnetic washing station 40 has a plurality of magnets fixed in position relative to each other. In a particular embodiment, the magnetic washing station 40 has two permanent rectangular magnets 50, 51, i.e., a first magnet 50 generating a first magnetic field, and a second magnet 51 generating a second magnetic field. In a particular embodiment of the invention, the first magnet 50 and the second magnet 51 have different strengths and generate magnetic fields of unequal magnitude. In one embodiment according to the invention, the first magnet 50 is stronger than the second magnet 51, i.e., the magnetic field generated by the first magnet 50 is greater in magnitude than the magnetic field generated by the second magnet 51. For example, the first magnet 50 may be 1-5 times as strong as the second magnet 51, preferably 1-2 times as strong. In a particular embodiment, referring still to FIG. 3, the magnets 50, 51 are mounted vertically and parallel to each other, with like poles of the magnets 50, 51 facing each other and separated by an air gap 53. The gap 53 separating the first magnet 50 from the second magnet 51 is in the range of one-sixteenth inch to 40 inches, in particular, 1.5 to 2.5 inches. In another embodiment, the gap 53 is determined to be 2.5 times to 1000 times the diameter of the probe 10.

In one embodiment according to the invention, the magnets 50, 51 are NeFeB magnets with magnetic faces 2.8 inches high and 0.5 inches wide. The stronger or first magnet 50 is the capture or immobilizing magnet and is about 1 inch thick along the direction of magnetization, and has remanence Br=13.1 kG. The weaker or second magnet 51 is the resuspend magnet and is about 0.2 inches thick along the direction of magnetization and has remanence Br=11.4 kG. In this embodiment, the air gap indicated by arrow 53 between the face of the strong magnet 50 and the face of the weak magnet 51 is 1.95 inches.

The flux density Bx a distance X from the face of a rectangular magnet of remanence Br, length L in the direction of magnetization, and face dimension A by B, is given by $$B_x = \frac{B_r}{\pi}\left(\tan^{-1}\frac{AB}{2X\sqrt{4X^2 + A^2 + B^2}} - \tan^{-1}\frac{AB}{2(L+X)\sqrt{4(L+X)^2 + A^2 + B^2}}\right)$$

For magnets 50 and 51 arranged as described above with like poles facing each other so that the magnetic forces from the two magnets are opposed in direction, the resultant flux density at any point on the central axis between the magnets is calculated as the algebraic sum of the flux densities from each individual magnet.

Figure 4A:
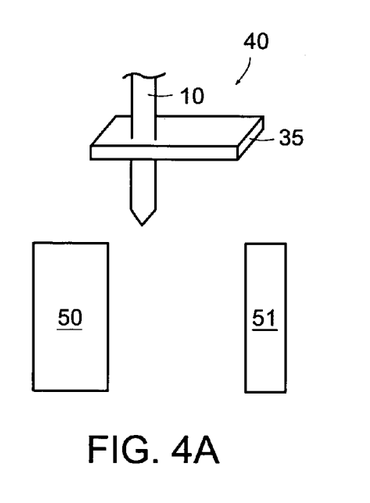
FIGS. 4A-4D illustrate various positions of the probe as the probe is moved by the transport stage.
Figure 4B:
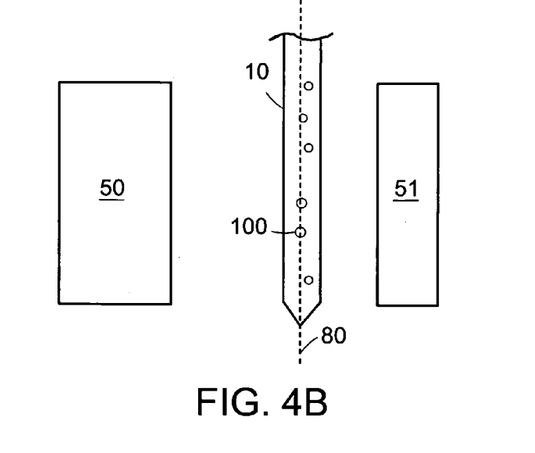

According to one embodiment of the invention, illustrated in FIG. 4A, the transport stage 35 moves the probe 10 from a sample station (not shown) to a position above the magnetic washing station 40. Referring now to FIG. 4B, the probe 10 is lowered by the transport stage 35 to a neutral position 80 between the first magnet 50 and the second magnet 51. The neutral position 80 is a position along a line drawn perpendicular to the face of the first magnet 50 and the face of the second magnet 51 where the resultant magnetic force on a magnetizable particle 100 is zero in the resultant magnetic field B generated by the first magnet 50 and the second magnet 51. As illustrated in FIG. 4B, the neutral position 80 is a position of the probe 10 in the magnetic washing station where the probe 10 is closer to the weaker magnet 51, i.e., the magnet generating a weaker magnetic field, for example as shown in FIG. 4B, than to the stronger first magnet 50.

Figure 4C:
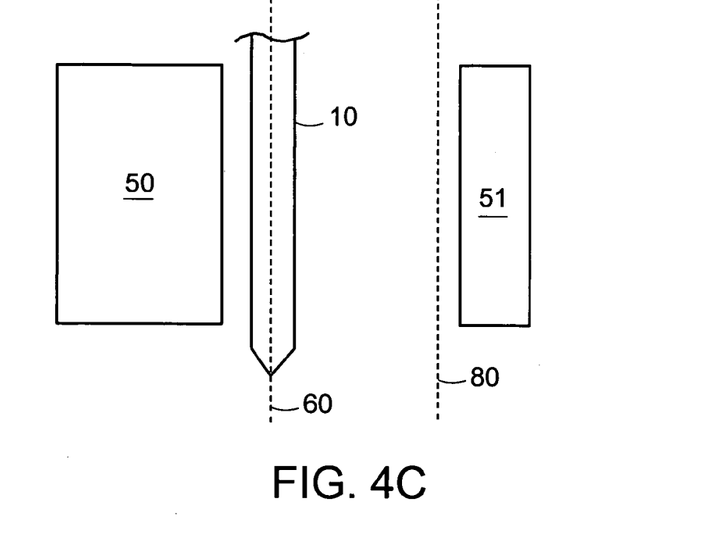
Figure 4D:
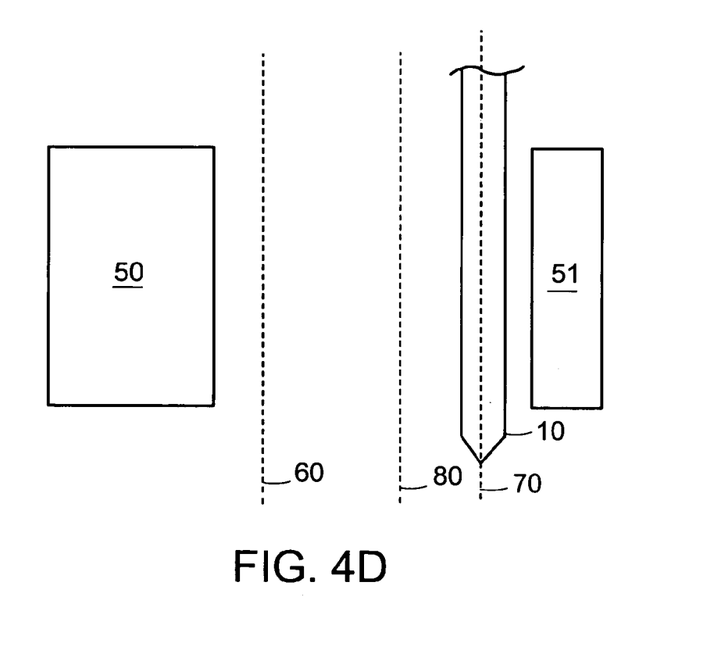

In one embodiment of the invention, illustrated in FIG. 4C, the transport stage 35 moves the probe 10 from the neutral position 80 to a capture position 60. The capture position 60 is adjacent the stronger magnet 50 where the strength of the magnetic field of the first magnet 50 relative to the second magnet 51 is greatest. In another embodiment of the invention illustrated in FIG. 4D, the transport stage 35 moves the probe 10 from the capture position 60 to a resuspend position 70. The probe 10 in the resuspend position 70 is closer to the second magnet 51 than is the probe 10 in the capture position 60 or the neutral position 80. In the resuspend position 70, the force of the magnetic field generated by the second magnet 51 is greater than the force of the magnetic field on a magnetizable particle 100 in the probe 10 generated by the first magnet 50. The overall force of the magnetic field is closer to zero in the resuspend position 70 than in the capture position 60.

In a particular embodiment according to the invention, the capture position 60 is 4.2 mm from the first magnet 50, the neutral position 80 is 22 mm from the second magnet 51, and the resuspend position 70 is 14 mm from the second magnet 51.

Figure 6A:
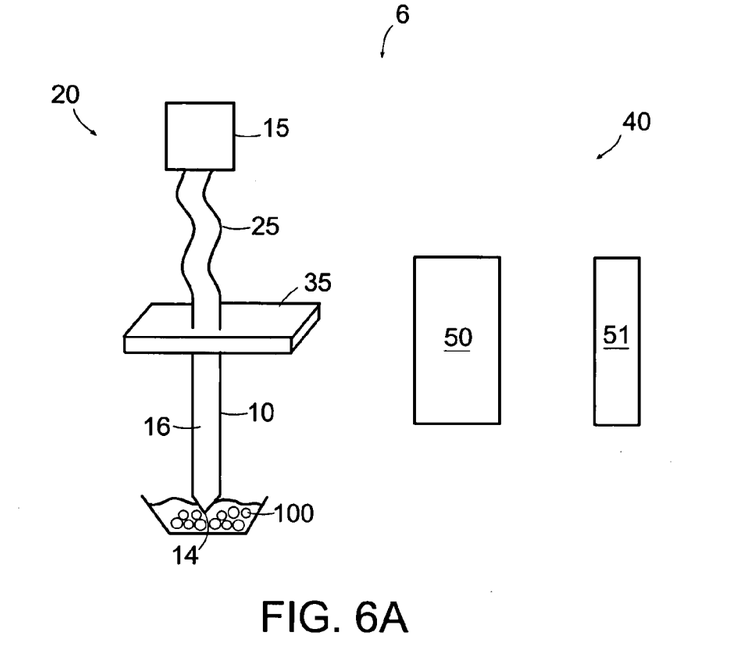
FIGS. 6A-6B illustrate the steps according to one embodiment of the invention for aspirating a sample with magnetizable beads into the probe.
Figure 6B:
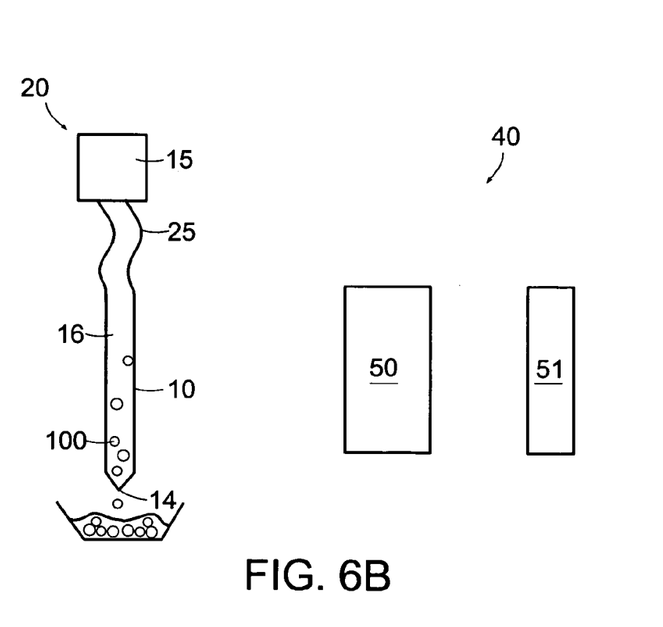

In another aspect, the invention is a method for immobilizing and washing magnetizable beads 100 in, for example, an automated instrument for performing an immunoassay. In one embodiment according to this aspect of the invention, the probe 10 is positioned at the sampling station 20, illustrated in FIG. 6A, at a position external to the magnetic washing station 40, and the sample end 14 of the probe 10 is lowered into a container such as a well in a microtiter plate until the sample end 14 of the probe 10 meets a fluid sample containing magnetizable particles 100. Referring now to FIG. 6B, in one embodiment according to this aspect of the invention, negative pressure generated by the dilutor assembly 15 causes an aliquot of fluid containing magnetizable particles 100 to be aspirated through the sample end 14 of the probe 10 and into the reservoir 16 of the probe 10. The magnetizable particles 100 are made from a material that may be attracted to a magnet. Such materials include, for example, iron, iron oxide and other such materials known to the skilled person. In a particular embodiment, the particle 100 is a magnetizable latex particle having an iron oxide core surrounded by a polystyrene shell that is coated with a polymer bearing functional groups to which an antibody, or variants thereof, can be attached, for example, 280 nanometer Dynabeads™ M-280 Sheep anti Mouse IgG, (DYNAL, Inc., Lake Successful, N.Y.). Alternatively, the magnetizable particles 100 may be paramagnetic particles, typically 1-20 μm in size having a composition including ion oxides and various other materials, e.g., agarose or cellulose which may also have functional group, e.g., aminosilanes, for antibody attachment (Advanced Magnetics, Inc., Cambridge, Mass.). The fluid in which the magnetizable particle 100 is suspended may be a body fluid, such as blood, containing an analyte of interest, a wash fluid, a diluent, or a fluid containing a visualant such as fluorescein, rhodamine, gold particles, horseradish peroxidase, isoluminol, a labelled molecule such as a labelled antibody, an unlabelled antibody, variants thereof, or other compounds directed to the analyte of interest.

Probe Positions and the Relative Force BdelB on the Magnetizable Particles

Figure 7A:
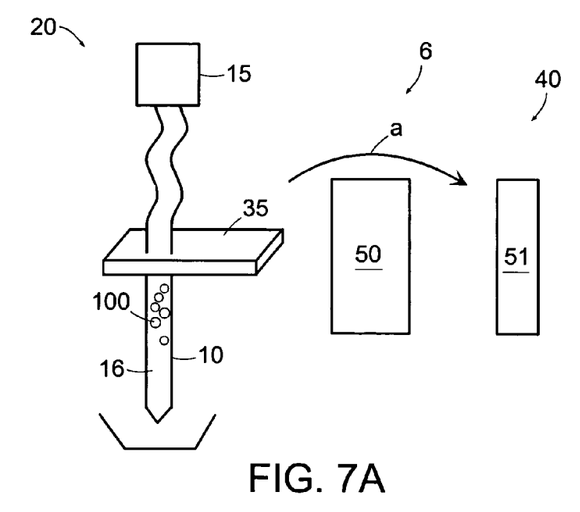
FIG. 7A illustrates one embodiment of the transport stage joined to the probe positioned in the sampling station.
Figure 7B:
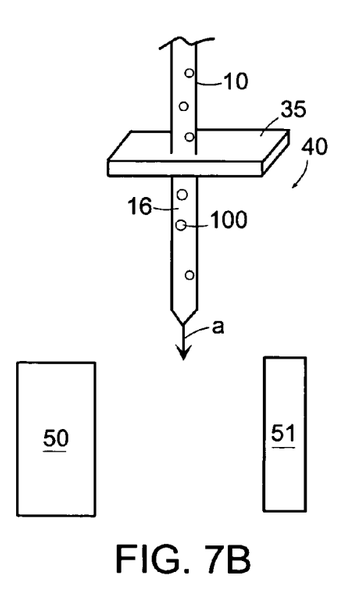
FIG. 7B illustrates the transport stage joined to the probe positioned over the magnetic washing station.
Figure 7C:
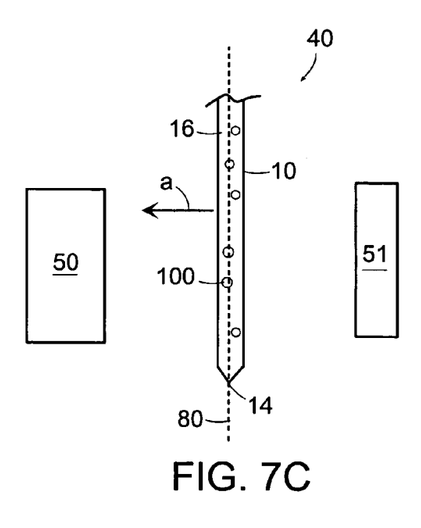
FIG. 7C illustrates one embodiment of the probe in the neutral position of the magnetic washing station.

In one embodiment of the invention referring to FIG. 7A, the probe 10 holding the magnetizable particles 100 and the sample fluid in the probe reservoir 16 is moved by the transport stage 35 from the sampling station 20, as indicated by arrow (a), to a position above the magnetic washing station 40, illustrated in FIG. 7B. Referring to FIG. 7B, the transport stage 35 moves the probe 10 as indicated by the arrow (a) into the neutral position 80 of the magnetic washing station 40, illustrated in FIG. 7C, such that the probe reservoir 16 is positioned in the area between the first magnet 50 and the second magnet 51 and the sample end 14 of the probe 10 is substantially outside of the magnetic field generated by the first magnet 50 and the second magnet 51.

Figure 5:
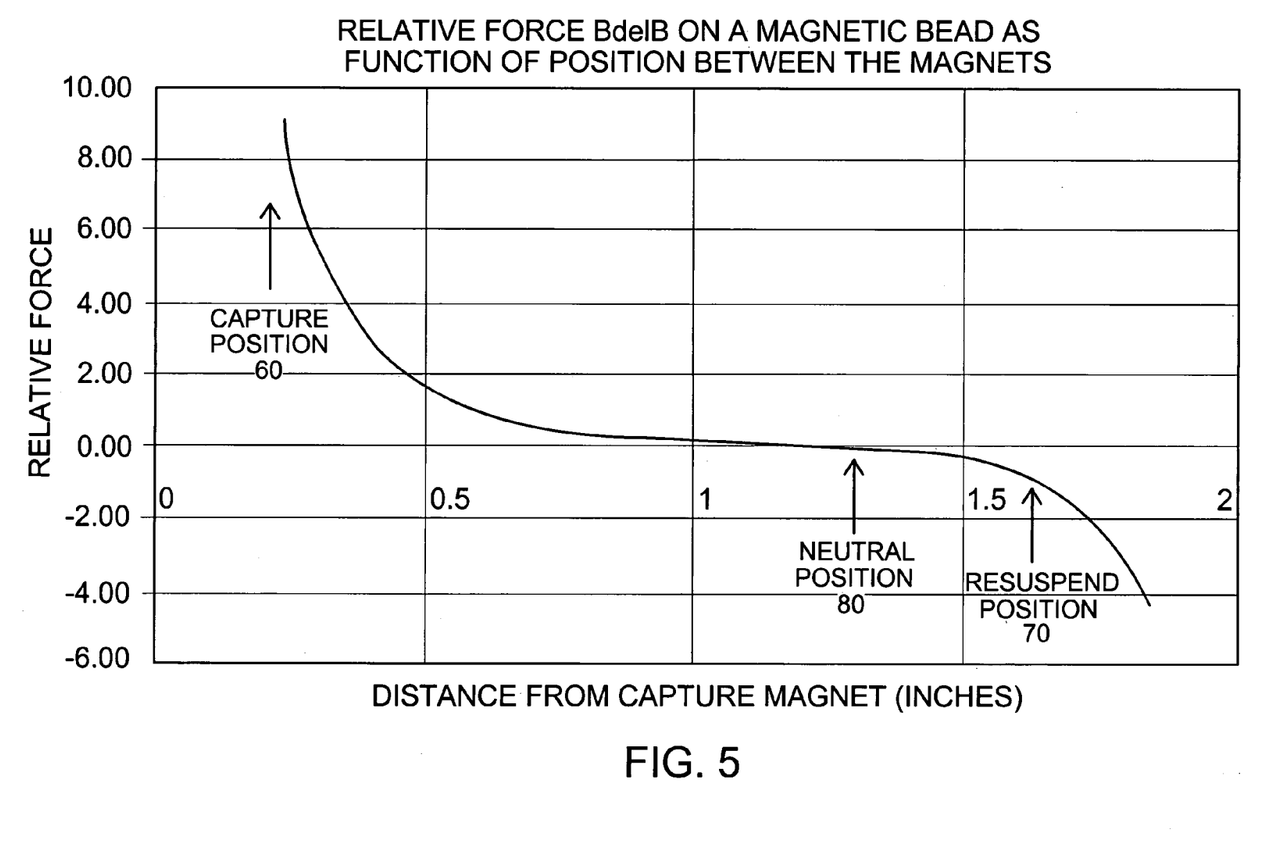
FIG. 5 is a graphic illustration of the relative force on a magnetizable bead as a function of the position of the bead between two magnets.

The calculated relative force on a magnetizable particle in a magnetic field B between magnet 50 and magnet 51 is proportional to BdelB, the product of the field strength times the field gradient. Referring to FIG. 5, the calculated relative force on a magnetizable particle 100 is graphically illustrated as a function of the neutral position 80 of the probe 10 in the magnetic washing station 40. The relative force BdelB on a magnetizable particle 100 in the neutral position 80 is zero, i.e., the relative force of the resultant magnetic fields generated by the first magnet 50 and the second magnet 51 in the neutral position 80 does not favor movement of the magnetizable particle 100 toward the first magnet 50 or the second magnet 51.

Figure 7D:
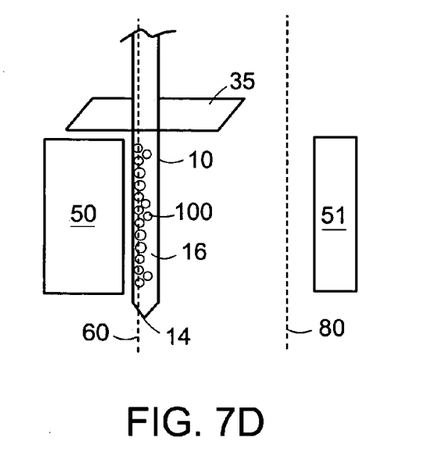
FIG. 7D illustrates one embodiment of the probe in the capture position of the magnetic washing station.

Referring again to FIG. 7C, the transport stage 35 joined to the probe 10 holding the magnetizable particles 100 in the probe reservoir 16, moves the probe 10 in a horizontal plane as indicated by arrow (a) from the neutral position 80 into the capture position 60. Referring now to FIG. 7D, the capture position 60 is adjacent the first magnet 50 when the magnetizable particles 100 are in the capture position 60, they are positioned in the magnetic field of greatest magnitude generated by the first magnet 50.

Referring again to the graph in FIG. 5, in the capture position 60 the calculated relative force on a magnetizable particle 100 is a function of the capture position 60 of the probe 10 in the magnetic washing station 40. The relative force BdelB generated by the first magnet 50 and the second magnet 51 on a magnetizable particle in a position between the neutral position 80 and the capture position 60 favors movement of the magnetizable particle 100 in the direction of the first magnet 50. FIG. 5 illustrates that the relative force BdelB in the (positive) direction of the first magnet 50 is maximal in the capture position 60.

Figure 7E:
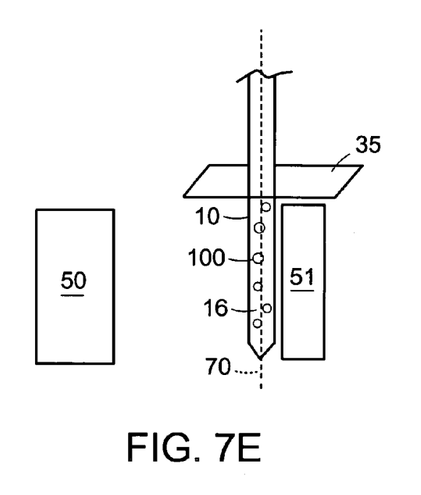
FIG. 7E illustrates one embodiment of the probe in the resuspend position of the magnetic washing station.

Referring now to FIG. 7E, in one embodiment according to the invention, the transport stage 35 joined to the probe 10 holding the magnetizable particles 100 in the probe reservoir 16, moves the probe 10 in a horizontal plane from the capture position 80 into the resuspend position 70. The resuspend position 70 is closer to the second magnet 51 than the neutral position 80 or the capture position 60.

Referring again to FIG. 5, in the capture position 60 the calculated relative force on a magnetizable particle 100 is graphically illustrated as a function of the resuspend position 70 of the probe 10 in the magnetic washing station 40. The relative force BdelB generated by the first magnet 50 and the second magnet 51 on a magnetizable particle 100 in a position between the neutral position 80 and the second magnet 51 favors movement of the magnetizable particle 100 in the direction of the second magnet 51. FIG. 7E illustrates the resuspend position 70 is any position between the neutral position 80 and the second magnet 51 where the relative force BdelB is in the direction of the second magnet 51.

Figure 7F:
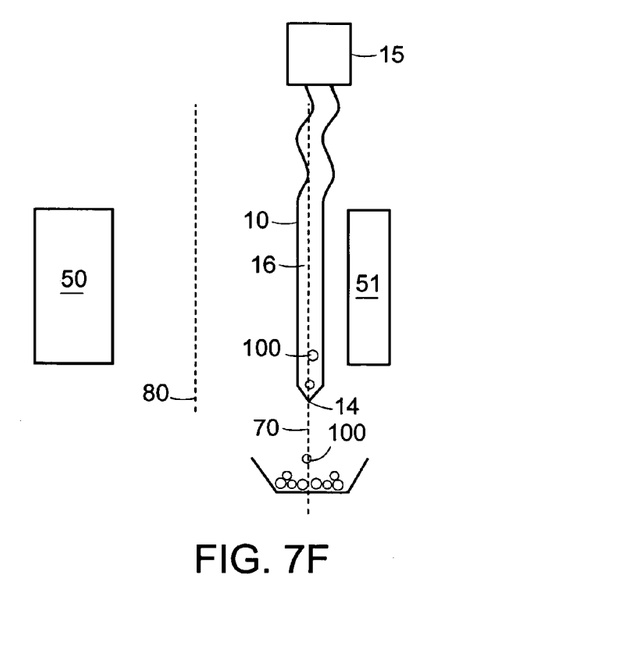
FIG. 7F illustrates one embodiment for dispensing the magnetizable particles from the probe reservoir through the probe sample end into a container.

Referring now to FIG. 7F, in one embodiment according to the invention, while the probe 10 is in the resuspend position 70, the dilutor assembly 15 expels the magnetizable particles 100 from the probe reservoir 16 through the sample end 14 of the probe 10 into a container.

Figure 8A:
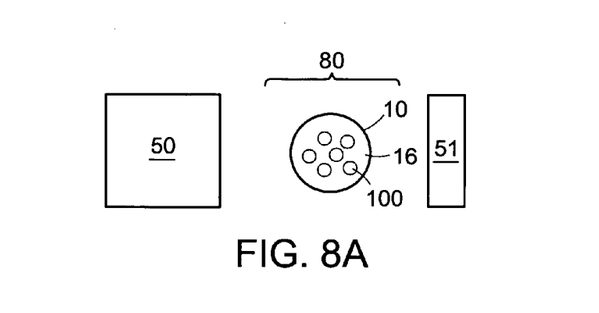
FIG. 8A illustrates the distribution of the magnetizable particles in the probe reservoir when the probe is in the neutral position in the magnetic washing station as viewed from the top of the magnetic washing station.
Figure 8B:
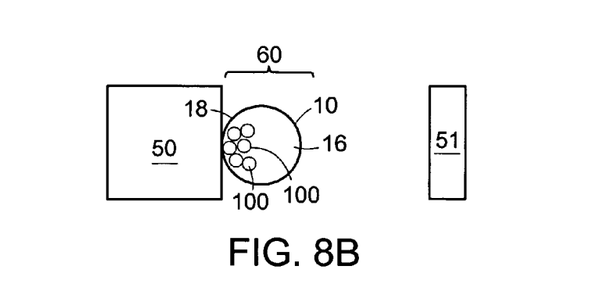
FIG. 8B illustrates the distribution of magnetizable particles when the probe is in the capture position in the magnetic washing station as viewed from the top of the magnetic washing station.
Figure 8C:
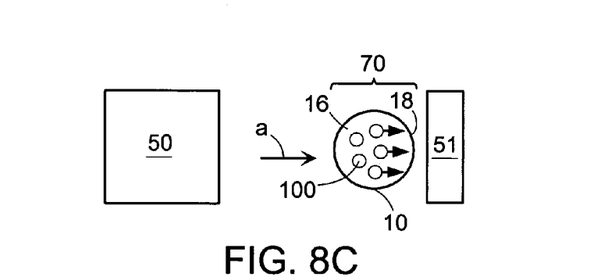
FIG. 8C illustrates the distribution of magnetizable particles when the probe is in the resuspend position in the magnetic washing station, as viewed from the top of the magnetic washing station.

The Effect of BdelB in the Positions of the Probe on the Distribution of the Magnetizable Particles in the Probe Reservoir FIGS. 8A-8C illustrate the distribution of the magnetizable particles 100 in the probe reservoir 16 when the probe 10 is in the probe neutral position 80, the probe capture position 60, and the probe resuspend position 70. Illustrated in FIG. 8A, as viewed from the top of the probe 10, in the neutral position 80 the magnetizable particles 100 are distributed randomly in the fluid medium of the probe reservoir 16. Referring now to FIG. 8B, in the capture position 60, the magnetizable particles 100 move from their free random distribution in the probe neutral position, to an immobilized position on the inside of the wall 18 on the side of the probe 10 that is closest to the first magnet 50. Referring now to FIG. 8C, in the resuspend position 70, the magnetizable particles 100 move away from their immobilized position on the side of the probe 10. With increasing dwell time in the resuspend position 70, the magnetizable particles 100 move away from the wall 18 where the particles 100 were immobilized in the capture position 60, and become suspended and dispersed in the fluid medium of the probe reservoir 16. The dwell time is brief enough to prevent the particles from being captured on the opposite side of the probe wall 18. Thus, by applying a magnetic force to actively move the immobilized magnetizable particles 100 away from the wall 18 of the probe 10, the invention described herein has several advantages over known devices that resort to steps that repeatedly expel and aspirate the magnetizable particle mixture in and out of the probe 10 through the probe sample end 14 in order to mix and resuspend the magnetizable particles 100 in the fluid medium. For example, the invention described herein minimizes the volume of fluid required to wash the magnetizable particles 100 because the particles 100 are resuspended in the wash fluid without requiring the step-by-step addition of successive volumes of wash fluid in order to flush the particles 100 from the probe lumen. The washing step described herein is faster than washing steps that repeatedly expel and aspirate the magnetizable particle mixture in and out of the probe. Aerosolizing the wash fluid is also minimized according to the method of the invention because it is not necessary to forcefully expel the particles in the wash fluid from the probe in order to resuspend the particles. Minimizing aerosol is particularly important when body fluids which may harbor pathogens are sampled by the probe.

Figure 9:
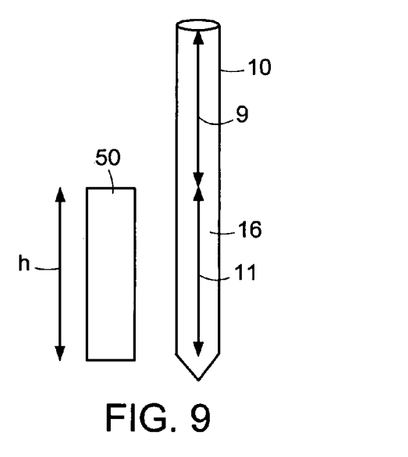
FIG. 9 illustrates one embodiment of the probe according to the invention.

In yet another embodiment according to the invention, immobilization of the magnetizable particles 100 held within the probe reservoir 16 is accomplished by a tandem capture method. In this embodiment, the length of the reservoir 16 in probe 10, illustrated in FIG. 9, is the sum of the length of the first portion 11 of the probe reservoir 16 which corresponds to the height h of the first magnet 50, plus the length of the second portion 9 of the probe reservoir 16 which corresponds to the length of the probe reservoir 16 in excess of the length of the first portion 11.

In the tandem capture method, magnetizable beads 100 are aspirated into and fill the length of the probe reservoir 16. The probe reservoir is moved adjacent the first magnet 50 into the capture position 60. The magnetizable beads 100 in the first portion 11 are in the magnetic field of the first magnet 50. The magnetizable beads 100 in the first portion 11 of the probe reservoir 16 are immobilized by the magnetic field of the first magnet 50 on the inner wall of the first portion 11 of the probe reservoir 16. The magnetizable beads 100 in the second portion 9 of the probe reservoir 16 are introduced by the dilutor assembly 15 from the second portion 9 into the first portion 11. Once the beads 100 from the second portion 9 are in the magnetic field of the first magnet 50, the beads 100 are immobilized on the inner wall 18 of the first portion 11 of the probe reservoir 16.

Figure 10A:
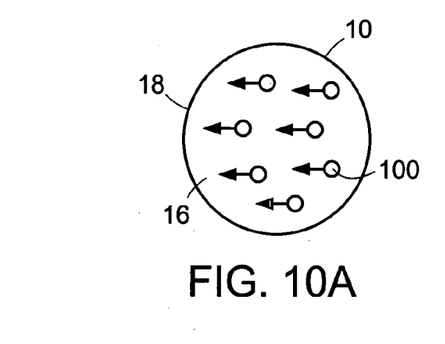
FIG. 10A illustrates one embodiment of a cross-section of the probe and the distribution of magnetizable particles in the probe reservoir when the probe is moved from the neutral position to the capture position in the magnetic washing station.
Figure 10B:
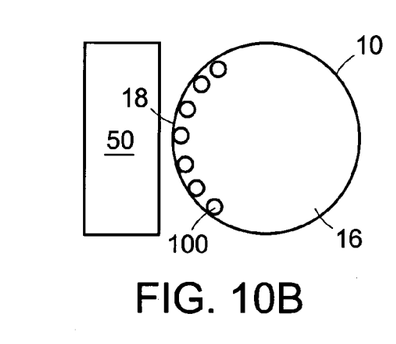
FIG. 10B illustrates the probe and the position of the magnetizable particles following a short dwell time in the capture position in the magnetic washing station.
Figure 10C:
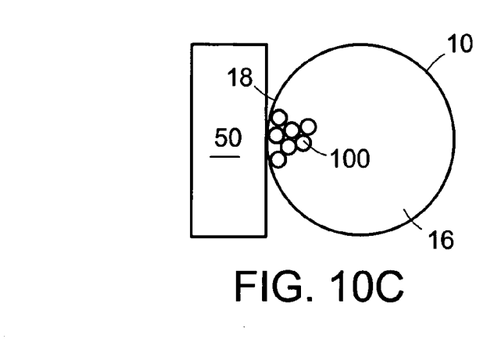
FIG. 10C illustrates the probe and the position of the magnetizable particles when the dwell time of the probe in the capture position is longer than the dwell time of the probe in the capture position illustrated in FIG. 10B.

The Effect of Probe Shape on Distribution of the Magnetizable Particles in the Capture Position The shape of the probe 10 in cross-section may vary from round to polygonal. In one embodiment of the invention, the probe 10 has a round cross section as shown in FIGS. 10A-10C. The magnetizable particles 100 are randomly distributed in the probe reservoir 16 when the round probe 10 is in the neutral position 80, illustrated in FIG. 10A. When the round probe 10 is moved from the neutral position 80 to the capture position 60, the magnetizable particles 100 tend to move toward the rectangular magnet 50 as indicated by the arrows shown in FIG. 10A. Accordingly, the magnetizable particles 100 accumulate on the portion of the inside circumference of the wall 18 that is closest to the first magnet 50, illustrated in FIG. 10B. With increasing dwell time in the capture position 60, the magnetizable particles 100 tend to migrate to and aggregate at a point on the inside wall 18 of the probe 10 closest to the first magnet 50, as illustrated in FIG. 10C.

Figure 11A:
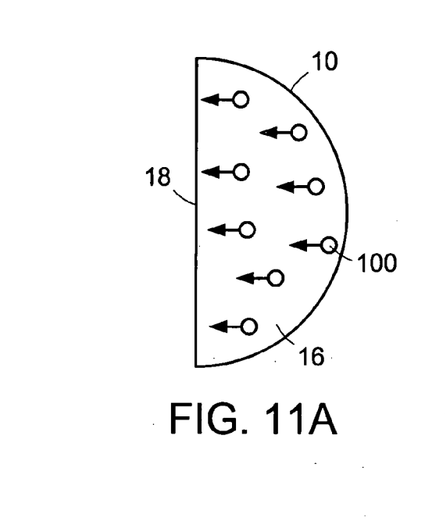
FIG. 11A illustrates another embodiment of a cross-section of the probe and the distribution of the magnetizable particles in the probe reservoir when the probe is moved from the neutral position to the capture position in the magnetic washing probe.
Figure 11B:
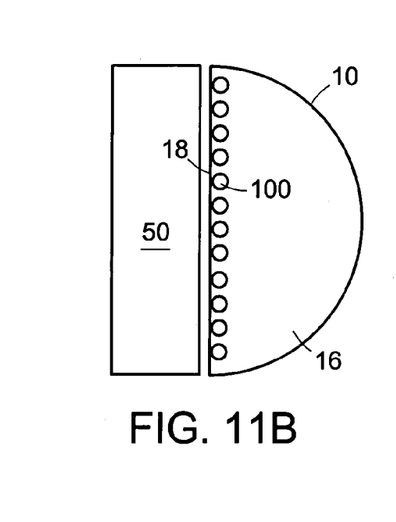
FIG. 11B illustrates the probe and the position of the magnetizable particles following a short dwell time in the capture position in the magnetic washing station.
Figure 11C:
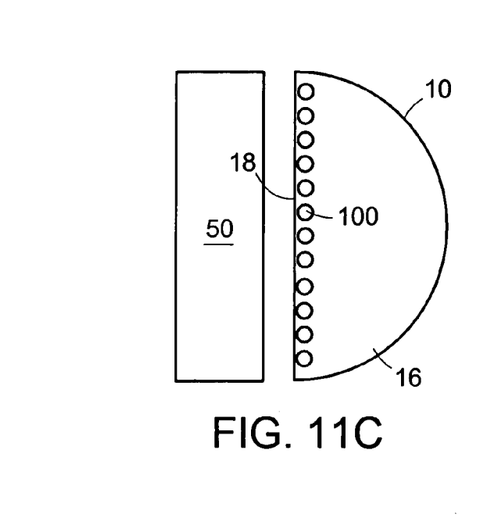
FIG. 11C illustrates the probe and the position of the magnetizable particles when the dwell time of the probe in the capture position is longer than the dwell time of the probe in the capture position illustrated in FIG. 11B.

In another embodiment according to the invention, the probe 10 has a "D" shape cross-section as shown in FIGS. 11A-11C. In a particular embodiment, illustrated, for example, in FIG. 11A, the wall 18 of the probe reservoir 16 closest to the rectangular magnet 50 is substantially flat, i.e., a cross section through the probe reservoir 16 is "D" shaped with the flat side of the "D" nearest the first magnet 50. With a "D" shape probe 10, the magnetizable particles 100 are randomly distributed in the probe reservoir 16 when the probe 10 is in the neutral position 80, illustrated in FIG. 10A. When the "D" shaped probe 10 is moved from the neutral position 80 to the capture position 60, the magnetizable particles 100 tend to distribute uniformly across the inside flat surface of the wall 18 of the probe, illustrated in FIG. 11B. With increasing dwell time in the capture position 60, the magnetizable particles 100 tend to remain distributed relatively uniformly, as described above, on the inside wall 18 of the probe 10 closest to the rectangular magnet 50, illustrated in FIG. 11C.

The Washing Step in the Capture Position

In one aspect, the invention is a method for washing a magnetizable particle 100 used in an assay for detecting an analyte, such as in an immunoassay. In one embodiment, an antibody directed to the analyte of interest is bound to a magnetizable particle 100, such as a magnetizable bead, and mixed with an aliquot of a sample, such as blood. In the sample station 20, the sample and magnetizable beads 100 are aspirated through the sample end 14 of the probe 10 into the probe reservoir 16. The probe 10 holding the sample and the magnetizable beads 100 is raised by the transport stage 35 and moved to the magnetic washing station 40 over the two magnets 50, 51. The probe 10 is lowered by the transport stage 50 between the two magnets 50, 51 into the neutral position 80. The probe 10 is then moved horizontally by the transport stage 35 into the capture position 60. The magnetizable beads 100 bound to the antibody directed to the analyte of interest in the blood sample are immobilized in the probe reservoir 16 by the magnetic field of the first magnet 50. A wash fluid is introduced by the dilutor assembly 15 through the tubing 25 and into the top 12 of the probe 10 and expelled through the sample end 14. The probe is moved horizontally to the resuspend position 70 where the magnetizable beads 100 are resuspended and mixed in the fluid before the mixture containing the magnetizable particles 100 is expelled through the sample end 14 of the probe 100. The probe 100 is moved by the transport stage 35 back to the sample station 20 to pick up another sample.

The direction of movement of the probe in each step of the method is intended to be exemplary and not limited to only that which is specifically recited.

Changes and modification may be made to the invention without departing from the scope and spirit of the invention. Accordingly, the particular combinations of parts described and illustrated herein is intended to represent only an illustrative embodiment of the invention, and is not intended to serve as limitations of alternative embodiments.

What is claimed is:

1. A device for manipulating a magnetizable particle suspended in a solution, comprising:
   a first magnet;
   a second magnet; and
   a probe for holding and transporting said magnetizable particle comprising an open top and an open bottom, wherein said probe is transportable through a plurality of positions between said first magnet and said second magnet in a horizontal direction for manipulating said magnetizable particle, wherein said magnetizable particle is resuspended in one of said probe positions, and wherein the strength of said first magnet is weaker than the strength of said second magnet.

2. The device according to claim 1 further comprising a dilutor assembly, wherein said dilutor assembly introduces a fluid into the open top of the probe, and wherein the open top of the probe is opposite to the open bottom of said probe.

3. The device according to claim 1 wherein said probe further comprises a thermal control element.

4. The device according to claim 1 wherein said probe further comprises a liquid level sensing element.

* * * * *